US006224875B1

(12) United States Patent
Bombardelli et al.

(10) Patent No.: US 6,224,875 B1
(45) Date of Patent: May 1, 2001

(54) *TANACETUM PARTHENIUM* EXTRACT AND METHOD OF OBTAINING SAME

(75) Inventors: Ezio Bombardelli; Paolo Morazzoni, both of Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 09/385,513

(22) Filed: Aug. 27, 1999

(30) Foreign Application Priority Data

Jun. 3, 1999 (IT) .............................................. MI99A1244

(51) Int. Cl.⁷ ..................................................... A61K 35/78
(52) U.S. Cl. ......................... 424/195.1; 514/816; 514/885
(58) Field of Search ......................... 424/195.1; 514/885, 514/816

(56) References Cited

U.S. PATENT DOCUMENTS 4,758,433 * 7/1988 Johnson et al. .
5,384,121 * 1/1995 Rhodes .
5,466,451 * 11/1995 Beuscher et al. .

FOREIGN PATENT DOCUMENTS

9348241 * 4/1994 (AU) .

OTHER PUBLICATIONS

Sumner et al. Biochem. Pharmacol. vol. 43 (11), pp. 2313–2320, 1992.*
Heptinstall et al. ACS Symp. Ser. vol. 691 (Phytomedicines of Europe), pp. 158–175, 1998.*
Dornelles et al. Rev. Bras. Farm. vol. 79 (1/2), pp. 42–44, abstract enclosed, 1998.*
Lamminpaa et al. Contact Dermatitis, vol. 34 (5), pp. 330–335, abstract enclosed, 1996.*
Weerdt et al. Phytomed. vol. 3 (3), pp. 225–230, abstract enclosed, 1996.*
Barsby et al. Planta Med. vol. 59, pp. 20–25, 1992.*
Hausen et al. Acta Derm.–Venereol. vol. 63 (4), pp. 308–314, abstract enclosed, 1983.*
Hausen, B.M. Dermatosen in Beruf und Umwelt. vol. 29 (1), pp. 18–21, abstract enclosed, 1981.*
Williams et al. Phytochem. vol. 38, No. 1, pp. 267–270, 1995.*

* cited by examiner

*Primary Examiner*—Christopher R. Tate
(74) *Attorney, Agent, or Firm*—Pennie & Edmonds LLP

(57) ABSTRACT

Extracts of Tanacetum parthenium with a reduced content of α-unsaturated γ-lactones, particularly of parthenolide, obtainable by elution on basic resins are disclosed.

The extracts of the invention have favourable pharmacological properties together with reduced risks of allergic reactions.

6 Claims, 1 Drawing Sheet

TANACETUM PARTHENIUM EXTRACT AND METHOD OF OBTAINING SAME

TECHNICAL FIELD

The present invention relates to a *Tanacetum parthenium* extract substantially free of α-unsaturated γ-lactones. The invention additionally relates to a process for the preparation of the extract and to pharmaceutical and cosmetic compositions containing a *Tanacetum parthenium* extract which is substantially free of parthenolide.

TECHNOLOGICAL BACKGROUND

Extracts of *Tanacetum parthenium*, a plant belonging to the family Asteracee/Composite, also known as Altamisa, Crisanthemum, Leucanthemum, *Pyrethrum parthenium* as well as under the common name "feverfew", have traditionally been used in the treatment of migraine, vertigo, arthritis, menstrual disorders, fever, toothache, stomach ache and insect bites. Extracts of *Tanacetum parthenium* contain various volatile oils having mono- and/or sesquiterpene components, flavonoids, tannins, and pyrethrin, as well as terpenoids of the family of sesquiterpene lactones known as germacranolides, guaianolides and eudesmanolides. These latter compounds are characterized by an α-unsaturated γ-lactone structure and comprise in particular the compounds known as parthenolide, 3-β-hydroxy-parthenoide, costunolide, 3-β-hydroxy-costunolide, artemorin, 8-α-hydroxy-estafiatin and chrysanthemonin. The presence of these sesquiterpene lactones is considered necessary for the extracts to achieve pharmacological activity (J. Pharm. Pharmacol. 1992, 44:391–395).

Particular attention has been focused on parthenolide, which is thought to be the fundamental active ingredient of these extracts, but which is also responsible for allergic reactions which can sometimes occur following treatment with the extracts of *Tanacetum parthenium* (See, for example, Arch. Dermatol. Forsch. 1975, 251 (3):235–44; Arch. Dermatol. Forsch. 1976, 255 (2):111–21; Contact Dermatitis, 1988, 38 (4):207–8; Am. J. Contact Dermatol. 1998–9 (1):49–50; Br. J. Dermatol. 1995, 132 (4):543–7). Extracts of *Tanacetum parthenium* containing parthenolide are disclosed in WO 94 06800; EP 0 553 658; WO 92 11857; GB 2,166,952; EP 98 041; WO 98 39018.

SUMMARY OF THE INVENTION

In a first embodiment the invention is directed to a *Tanacetum parthenium* extract which is substantially free of α-unsaturated γ-lactones. In a preferred embodiment, the content of α-unsaturated γ-lactone is below 0.2 wt %. More preferably, the α-unsaturated γ-lactones are present in an amount of no more than 0.1 wt. %.

In a further embodiment the extract is substantially free of parthenolide. Preferably the parthenolide content is below 0.2 wt. %, and more preferably below 0.1 wt. %.

In another embodiment, the invention is directed to a *Tanacetum parthenium* extract which is obtainable by a process comprising the steps of:

(a) extracting a quantity of plant material from an aerial portion of *Tanacetum parthenium* with a solvent selected from the group consisting of acetone, an alcohol and mixtures of acetone or an alcohol with water, to form a first extract;

(b) extracting the first extract with a hydrocarbon solvent to produce a second extract having a hydrocarbon phase and a non-hydrocarbon phase;

(c) evaporating the hydrocarbon phase from the second extract to form a first residue;

(d) extracting the non-hydrocarbon phase with a non-polar solvent to form a third extract;

(e) evaporating the non-polar solvent portion of the third extract to produce a second residue and redissolving the second residue in a water-alcoholic solution of acid;

(f) adding to the water-alcoholic solution a quantity of a strongly basic resin;

(g) eluting the resin with an alcohol solution and separating the eluate from the resin;

(h) treating the resin with an alcoholic or water-alcoholic solution of an acid;

(i) concentrating the alcoholic or water-alcoholic solution to form a third residue;

(j) extracting the third residue with a non-polar solvent to produce a fourth extract;

(k) evaporating the non-polar solvent from step (j) to form a fourth residue;

(l) combining the first and the fourth residues with the third extract to form a mixture;

(m) evaporating a liquid portion of the mixture to form a fifth residue; and (n) at least partially drying the fifth residue.

Still further, the invention is directed to a pharmaceutical composition containing an extract as described herein in admixture with a pharmaceutically acceptable carrier.

The invention is additionally directed to a process for forming an extract of *Tanacetum parthenium* substantially free of α-unsaturated γ-lactone which comprises the method steps set forth above.

DETAILED DESCRIPTION OF THE INVENTION

Figure 1:
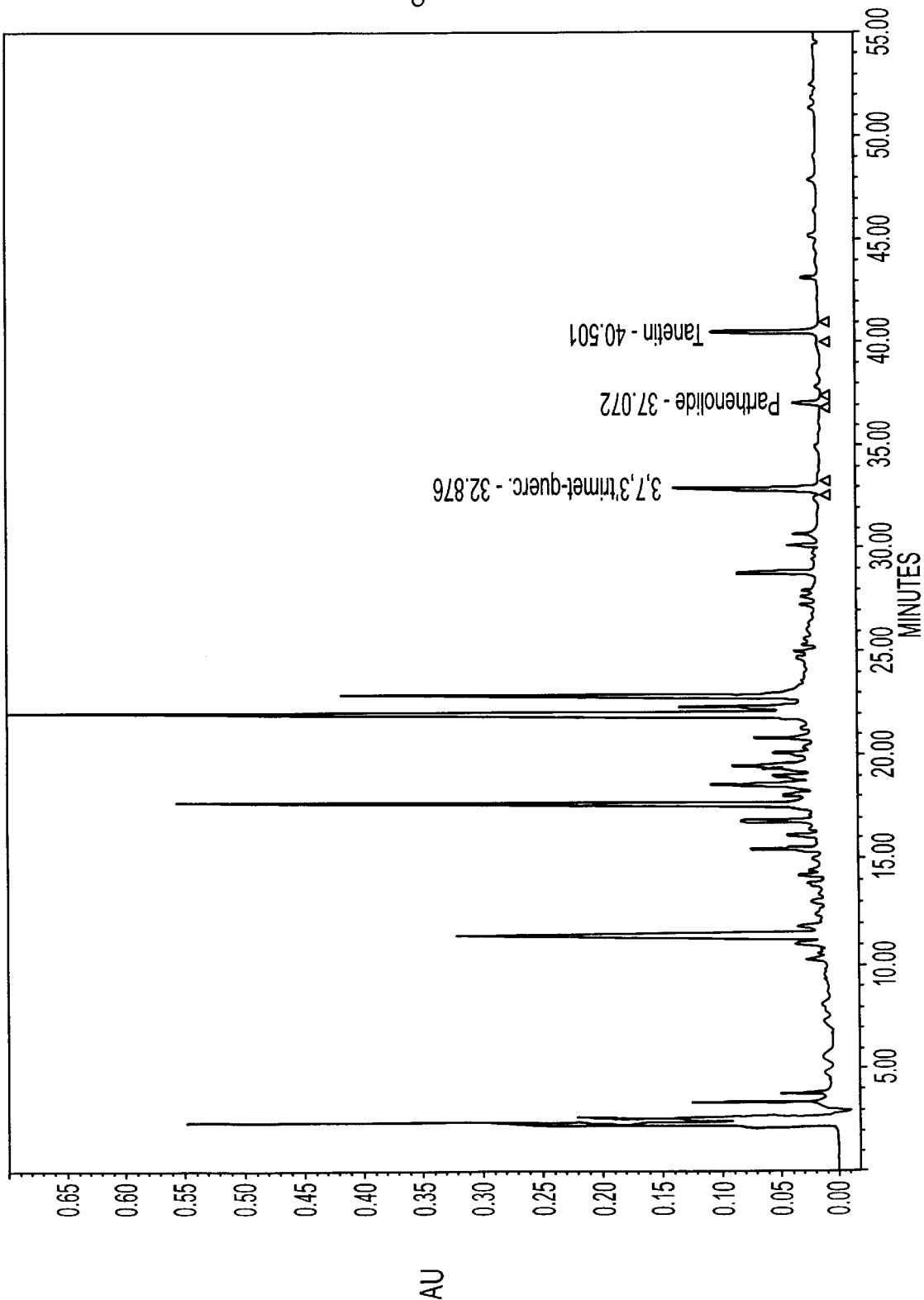
FIG. 1 illustrates a typical high pressure liquid chromatographic profile of an extract obtained in accordance with the invention.

The inventors have determined that *Tanacetum parthenium* extracts substantially free from α-unsaturated γ-lactones and, more particularly, substantially free from parthenolide, have interesting pharmacological properties, together with a remarkably reduced risk of allergic reactions.

The extracts of the invention can therefore be conveniently used as active ingredients for the preparation of a variety of pharmaceutical and oral cosmetic compositions.

"Substantially free from α-unsaturated γ-lactones" and "substantially free from parthenolide" as used herein mean an extract having a weight content of α-unsaturated γ-lactone or parthenolide, respectively, below about 0.2%, preferably below about 0.1%, more preferably below about 0.09% and most preferably below about 0.07%. All of these percentages, unless otherwise noted, refer to percent by weight.

The extract of the invention is obtained with the use of a process which comprises:

a) extracting a quantity of plant material from the aerial portion of the plant with acetone, alcohols or a mixture of these solvents with water;

b) extracting the material from step a) with a hydrocarbon solvent;

c) extracting the remaining non-hydrocarbon phase with a non-polar solvent;

d) evaporating the non-polar solvent extract and redissolving the residue in water-alcoholic solution, and then treating the redissolved residue with a strong basic resin;

e) eluting the resin with an alcohol and removing the eluted solution;

f) treating the resin with an alcoholic or water-alcoholic solution of an acid, concentrating the solution and extracting the resulting residue with a non-polar solvent;

g) evaporating the solvents the non-polar solvent from step f) to form a residue which is added to the residue from the evaporation of the hydrocarbon extract from step b) and to the acetonic or alcoholic phase obtained after the extraction with the non-polar solvent of step c)

h) evaporating the solvent and drying the remaining residue.

Parthenolide and the other related sesquiterpene lactones are removed from the extract since the strong basic resin surprisingly does not cause the opening of the lactone ring, which is recognizedly sensitive to basic hydrolysis. The flavone components having acid hydroxy groups are therefore retained by the resin, in contrast to parthenolide and related compounds which can therefore be removed.

The preferred solvents for the various extraction steps include, but are not limited to the following:

step a): acetone, methanol, ethanol or mixtures thereof with water;

step b): hexane, n-pentane, petroleum ether, ligroin;

step c): methylene chloride, chloroform, ethyl acetate, preferably methylene chloride;

step f): ethyl acetate.

"Alcoholic or water-alcoholic solvents" as those terms are used herein refer to methanol or methanol with water in percentages ranging from about 10 to about 80% by volume.

Basic resins preferred for use in the process of the invention are commercially available, for example, under the registered trademarks RELITE® 2A, and RELITE® 3A2, from Resindoin SRL, Milan, Italy, and DOWEX® 2 from the Dow Chemical Co., Midland, Mich. The invention is not limited to the use of these particular products, however.

In an alternate embodiment, the extract of the invention can be obtained by treatment of commercially available *Tanacetum parthenium* extracts produced in the conventional manner with strongly basic resins. Optionally, lipophilic components which could adversely interfere with the resin may first be extracted with the use of hydrocarbon solvents before treatment with the resins.

The content of $\alpha$-unsaturated $\gamma$-lactones or of parthenolide in the final extract may be determined with the use of high pressure liquid chromatography ("HPLC"). A typical HPLC profile of an extract obtainable by the process described herein is shown in FIG. 1.

The extract of the invention has favorable pharmacological properties together with a remarkably reduced risk of inducing allergic reactions. The preservation of the pharmacological properties characteristic of the conventional extracts of *Tanacetum parthenium*, despite the almost complete removal of the sesquiterpene lactones, is even more surprising in view of the presently available documented reports regarding the relationship between bioactivity and composition of the known extracts (J. Pharm. Pharmacol. 1992,44:391–395.).

More particularly, the extracts of the invention, which are substantially free from parthenolide, have antiplatelet, anti-inflammatory, analgesic and anti-migraine activities.

The invention also relates to pharmaceutical compositions containing, as an active ingredient, a therapeutically effective amount of the *Tanacetum parthenium* extract of the invention in admixture with suitable carriers or other excipients. Suitable carrier and excipient materials are well known to those of ordinary skill in this art; see, e.g., Remington's Pharmaceutical Sciences Handbook, Mack Pub. Co., New York, XVII ed.

More particularly, the compositions of the invention may contain from about 10 to about 500 mg of extract of the invention, more preferably from about 50–200 mg per unit dose and are administered 3–4 times a day, or as required. Suitable dosage forms include, but are not limited to tablets, capsules, powders, syrups, and suspensions and solutions. Oral administration is the preferred route, but other types of administration, such as topical administration and parenteral administration, are within the scope of the invention.

The compositions of the invention are particularly useful for the therapy and prophylaxis of migraine attacks, but these compositions are not limited to the aforementioned use.

EXAMPLES

The invention is described in greater detail in the following examples, which are provided only for purposes of illustration and are not to be considered as limiting the invention in any manner.

EXAMPLE 1

PREPARATION OF THE EXTRACT

Two kilograms of *Tanacetum parthenium* were extracted at 50–60° C. with 20 liters of 70% aqueous methanol. The extract was concentrated under vacuum to about 1 liter and diluted with an equal volume of methanol. The resulting solution was extracted with 3×2 liters of n-hexane. The hexane extract was evaporated to dryness under vacuum to yield about 30 g of residue (extract H). The water-methanolic solution was then extracted with 2×0.5 liters of methylene chloride. The organic phase was evaporated to dryness under vacuum to yield about 70 g of residue (extract DCM). The water-methanolic phase (extract HM) was set aside. The DCM extract was dissolved in 0.6 L of 90% methanol and treated under stirring with 0.6 liters of a strongly basic resin (RELITE® 2A) for three-four hours. The suspension was filtered under vacuum and the resin was washed with about 2 liters of 90% methanol. The methanolic solution, containing parthenolide and its congeners, was removed. The basic resin was then treated under stirring for one hour with 0.6 liters of methanol containing 65 ml of concentrated hydrochloric acid. The resin was filtered under vacuum and washed with a further 2.5 liters of methanol. The filtrate and the washings were combined, concentrated under vacuum to about 200 mL and extracted with 3×200 ml of ethyl acetate. The resulting extract (E.A.), containing the flavone components tanetin and congeners, was evaporated to dryness under vacuum, to obtain about 4 g of residue. The residues of the extracts H and E.A. were combined with the extract HM. The resulting solution was evaporated to dryness under vacuum and the solid residue was dried under vacuum at 50° C. to constant weight. About 490 g of extract of departhenolidized *T. parthenium* was obtained which contains as determined, by HPLC analysis, (column Zorbax SB C18; eluent $H_2O$+0.01% TFA; B:MeCN+0.01% TFA; gradient A:B:90%–10%:10%–90%; flow 1 ml/min), a parthenolide content below 0.07%.

EXAMPLE 2
PHARMACOLOGICAL ACTIVITY

The experimental model of nitroglycerin-induced neuronal stimulation in the rat, described in Brain Research 1995,682:167–181; Brain Research 1995 695, 37–44 and in Neuropharmacol. 1997, 36(10);1417–1424, was used.

Nitroglycerin (a vasodilator commonly used to treat some cardiovascular disorders) can be used as a diagnostic tool in the study of migraine headache, since its administration causes a spontaneous-like attack in migraieurs. The nitroglycerin-induced attack is not immediate, but is delayed by some hours and is typically associated with accompanying symptoms such as nausea and photophobia. The vasodilating activity of organic nitrates, including nitroglycerin, arises from the metabolism to nitric oxide which is also reported to play a role as a neurotransmitter in the SNC. Neuronal stimulation rapidly activates the transcription of several proto-oncogenase, which, because of their rapid and transient induction, have been named immediate-early genes. Among them, c-fos is the most extensively studied and the protein encoded, Fos, is translocated to the nucleus where it persists for a few hours and can be detected immunoistochemically.

Experimental Procedures

Twenty-five male Sprague-Dawley rats were divided into groups containing 5 animals each. Two groups of animals (control and nitroglycerin) were injected with a vehicle alone (0.5% carboxymethylcellulose, 10 ml/kg) while the 3 other groups were treated orally for 3 days with a *Tanacetum parthenium* extract substantially free from parthenolide (TPPDE) at doses of 100 and 200 mg/kg and with a conventional (i.e., "regular") *Tanaceutum parthenium* extract (TPRE) at the same dosages, respectively.

One hour after the last administration, all the animals, except the control group, were treated subcutaneously with 10 ml/kg of the nitroglycerin.

Four hours after administration of the nitroglycerin, the rats were anaesthetized with sodium pentobarbital and perfused with fixative through the ascending aorta. The brains were quickly removed and postfixed in the same fixative overnight. Sections through the entire brain were cut at 50 μm on a freezing sliding microtome. Sections were serially collected in six wells containing old phosphate buffered saline (PBS) and processed for immunoistochemistry as free-floating sections.

The results are reported in Table I below which indicates the number of immunoreactive neurons (mean±the standard deviation) in the paraventricular nucleus of the hypothalamus (PVH), locus coeruleus (LC), and parabrachial nucleus (PBN) 4 hours after nitroglycerin administration.

TABLE I

| Treatment | PVH | LC | PBN |
|---|---|---|---|
| Control | 95.4 ± 43.1 | 47.0 ± 21.2 | 27.3 ± 15.2 |
| Nitroglycerin | 574.2 ± 298.5 | 334.3 ± 61.4 | 231.3 ± 89.4 |
| TPPDE (100) + nitroglycerin | 378.5 ± 182.9* | 200.5 ± 43.4* | 140.7 ± 64.6* |
| TPPDE (200) + nitroglycerin | 123.4 ± 74.5** | 87.5 ± 24.5** | 71.6 ± 28.6** |
| TPRE (200) + nitroglycerin | 569.7 ± 288.3 | 321.2 ± 49.1 | 228.3 ± 87.5 |

While the foregoing description represents the preferred embodiments of the present invention, it will be understood that various additions, modifications and substitutions may be made therein without departing from the spirit and scope of the present invention as defined in the accompanying claims.

What is claimed is:

1. A *Tanacetum parthenium* extract obtained by a process which comprises:
   (a) extracting a quantity of plant material from an aerial portion of *Tanacetum parthenium* with a solvent selected from the group consisting of acetone, an alcohol and mixtures of acetone or an alcohol with water, to form a first extract;
   (b) extracting said first extract with a hydrocarbon solvent to produce a second extract having a hydrocarbon phase and a non-hydrocarbon phase;
   (c) evaporating the hydrocarbon phase from said second extract to form a first residue;
   (d) extracting the non-hydrocarbon phase with a non-polar solvent to form a third extract;
   (e) evaporating the non-polar solvent portion of the third extract to produce a second residue and redissolving said second residue in a water-alcoholic solution of acid;
   (f) adding to said water-alcoholic solution a quantity of a strongly basic resin;
   (g) eluting said resin with an alcohol solution and separating a resultant eluate from said resin;
   (h) treating said resin with an alcoholic or water-alcoholic solution on an acid;
   (i) concentrating said alcoholic or said water-alcoholic solution to form a third residue;
   (j) extracting the third residue with a non-polar solvent to produce a fourth extract;
   (k) evaporating the non-polar solvent from step (j) to form a fourth residue;
   (l) combining the first and the fourth residues with the third extract to form a mixture thereof; and
   (m) evaporating a liquid portion of the mixture to form a fifth residue comprising an extract of *Tanacetum parthenium* which is substantially free of α-unsaturated γ-lactones.

2. The extract of claim 1 wherein said fifth residue is at least partially dried.

3. A pharmaceutical composition containing, as an active ingredient, the extract of claim 1, in an admixture with a pharmaceutically acceptable carrier.

4. A process for forming an extract of *Tanacetum parthenium* which is substantially free of a α-unsaturated γ-lactones, which process comprises:
   (a) extracting a quantity of plant material from an aerial portion of *Tanacetum parthenium* with a solvent selected from the group consisting of acetone, an alcohol and mixtures of acetone or an alcohol with water, to form a first extract;
   (b) extracting said first extract with a hydrocarbon solvent to produce a second extract having a hydrocarbon phase and a non-hydrocarbon phase;
   (c) evaporating said hydrocarbon phase from said second extract to form a first residue;
   (d) extracting the non-hydrocarbon phase with a non-polar solvent to form a third extract;
   (e) evaporating the non-polar solvent potion of the third extract to produce a second residue and redissolving said second residue in a water-alcoholic solution;
   (f) adding to said water-alcoholic solution a quantity of a strongly basic resin;
   (g) eluting said resin with an alcohol and separating a resultant eluate from said resin;

(h) treating said resin with an alcoholic or water-alcoholic solution of an acid;

(i) concentrating said alcoholic or said water-alcoholic solution to form a third residue;

(j) extracting said third residue with a non-polar solvent to produce a fourth extract;

(k) evaporating the non-polar solvent from step (j) to form a fourth residue;

(l) combining said first and said fourth residues with said third extract to form a mixture thereof; and (m) evaporating a liquid portion of said mixture to form a fifth residue comprising an extract of *Tanacetum parthenium* which is substantially free of $\alpha$-unsaturated $\gamma$-lactones.

5. The process of claim 4 which further comprises at least partially drying said fifth residue.

6. The *Tanacetum parthenium* extract obtained by the process of claim 4.

* * * * *